United States Patent [19]
Hiejima et al.

[11] Patent Number: 5,927,326
[45] Date of Patent: Jul. 27, 1999

[54] MULTI STAGE TYPE FLOW RATE SWITCHING DEVICE

[75] Inventors: Katsuhiro Hiejima; Yosuke Naoki, both of Osaka, Japan

[73] Assignee: Nissho Corporation, Osaka, Japan

[21] Appl. No.: 08/892,159

[22] Filed: Jul. 14, 1997

[30] Foreign Application Priority Data

Jul. 17, 1996 [JP] Japan .................................. 8-187682

[51] Int. Cl.⁶ .................................................. A61M 1/14
[52] U.S. Cl. ........................................... 137/601; 137/599
[58] Field of Search ..................................... 137/599, 601

[56] References Cited

U.S. PATENT DOCUMENTS

| | | | |
|---|---|---|---|
| 2,509,456 | 5/1950 | Saballus | 137/599 X |
| 3,010,316 | 11/1961 | Snyder | 137/599 X |
| 3,298,367 | 1/1967 | Bergman | 137/599 X |
| 3,788,602 | 1/1974 | Kitzie | 251/312 |
| 4,219,021 | 8/1980 | Fink | 128/214 B |
| 4,237,879 | 12/1980 | Genese | 128/214 G |
| 4,276,904 | 7/1981 | Jackson | 137/599 |
| 4,573,974 | 3/1986 | Ruschke | 604/81 |
| 4,643,224 | 2/1987 | Rung et al. | 137/599 X |
| 5,356,379 | 10/1994 | Vaillancourt | 604/80 |

FOREIGN PATENT DOCUMENTS 0 800 837 A2  10/1997  European Pat. Off. .

*Primary Examiner*—Stephen M. Hepperle
*Attorney, Agent, or Firm*—Kubovcik & Kubovcik

[57] ABSTRACT

A multi-stage type flow rate switching device is provided which simplifies switching of flow paths and which rarely causes erroneous operation. The multi-stage type flow rate switching device includes a constant flow rate path 2 and a variable flow rate path 3 arranged in parallel between a liquid medicine flow inlet port 1 and a liquid medicine flow outlet port 4 where the variable flow rate path 3 can change the flow rate by means of a three-way stopcock 33. Although the flow rate can be switched in four stages when one variable flow rate path 3 is arranged as shown by FIG. 1, the flow rate can be switched in further multi-stages by providing two or more of the variable flow rate paths 3.

7 Claims, 4 Drawing Sheets

5,927,326

MULTI STAGE TYPE FLOW RATE SWITCHING DEVICE

BACKGROUND OF THE INVENTION

1. Field of the Invention

The present invention relates to a flow rate switching device capable of switching a liquid flow rate in multi stages. More particularly, the present invention relates to a multi-stage type flow rate switching device capable of switching the flow rate of a liquid medicine in several stages by using a three-way stopcock.

The multi-stage type flow rate switching device according to the present invention is preferably used by being connected to a ballooned liquid medicine continuous injector (an injector where liquid medicine is filled in a balloon made of an elastic rubber material and liquid medicine is continuously injected over a period of many hours into blood vessels or the like by utilizing the force produced by contraction of the balloon as disclosed in, for example, Japanese Examined Patent Publication No. JP-B-6-83725) that is used as a means for continuously administering a liquid analgetic, anesthetic, antibiotic, or carcinostatic agent into blood vessels, hypodermic portions, epidural portions or the like in a small amount.

2. Description of Related Art

A three-way stopcock has conventionally been used in the medical field when a blood transfusion or a solution transfusion is carried out.

A three-way stopcock is typically constituted by a cylindrical portion having three branch tubes projecting in a T-like shape at the outer periphery of the cylindrical portion, a plug portion inserted in and rotatably attached to the cylindrical portion and having a liquid path in a T-like shape corresponding to the branch tubes of the cylindrical portion, and a lever attached to the plug portion for switching the flow paths.

Meanwhile, with respect to a variable small flow rate control device used in a ballooned liquid medicine continuous injector, a device comprising flow rate control tubes connected to a multi-way stopcock has already been proposed (Japanese Unexamined Patent Publication No. JP-A-5-84310). The device is constituted by a main body having a cylindrical valve chamber where one flow inlet port and at least three flow outlet ports are formed. A plug having a cylindrical valve portion is rotatably inserted into the valve chamber of the main body. A slit opened in a fan-like shape and slender holes in a straight tube shape extending opposedly in the radial direction from the base of the slit are formed in the valve portion and, even if the slender holes of the valve portion are connected to any of the flow outlet ports, the slit is connected to the flow inlet port.

However, according to the above-described flow rate control device, one flow rate control tube is necessary for each flow outlet port and various sizes of the flow rate control tubes are necessary. It is troublesome in view of production control and assembly operation to fabricate various sizes of flow rate control tubes and integrate them simultaneously. Also, the use thereof involves a drawback where the switch angle of the lever is decreased for a large number of switchings and the display is complicated whereby erroneous operation is liable to occur.

The present invention has been achieved as a result of an intensive study in view of the above-described situation and it is an object of the present invention to provide a multi-stage type flow rate switching device which simplifies switching of flow paths and rarely causes erroneous operation.

SUMMARY OF THE INVENTION

The inventors have determined, as a result of an intensive study, that flow rate switching operations can be facilitated and erroneous operation can be prevented by assembling a constant flow rate path and a variable flow rate path in parallel between a liquid medicine flow inlet port and a liquid medicine flow outlet port of a flow rate switching device and appropriately providing a three-way stopcock in the variable flow rate path.

That is, the present invention is directed to a multi-stage type flow rate switching device that includes a constant flow rate path and at least one variable flow rate path arranged in parallel between a liquid medicine flow inlet port and a liquid medicine flow outlet port where the flow rate of the variable flow rate path can be varied by a three-way stopcock.

The multi-stage type flow rate switching device may have the following construction. The liquid medicine flow inlet port is branched into three branch paths. One of the branch paths and the two remaining branch paths are respectively connected to the constant flow rate path and the variable flow rate path. Flow rate control tubes for controlling flow rate by resistance to flow are arranged in the constant flow rate path and the variable flow rate path which is arranged between the liquid medicine flow inlet port and the three-way stopcock. Alternatively, the liquid medicine flow outlet port is branched into three branch paths. One of the branch paths and the two remaining branch paths are respectively connected to a constant flow rate path and a variable flow rate path. Flow rate control tubes for controlling the flow rate by resistance to flow may be arranged in the constant flow rate path and the variable flow rate path which is arranged between the liquid medicine flow outlet port and a three-way stopcock.

The constant flow rate path and the variable flow rate path may preferably be accommodated in a housing having a liquid medicine flow inlet port and a liquid medicine flow outlet port at both ends thereof.

DETAILED DESCRIPTION OF THE PREFERRED EMBODIMENTS

Embodiments of the present invention are explained below with reference to the drawings.

Figure 1:
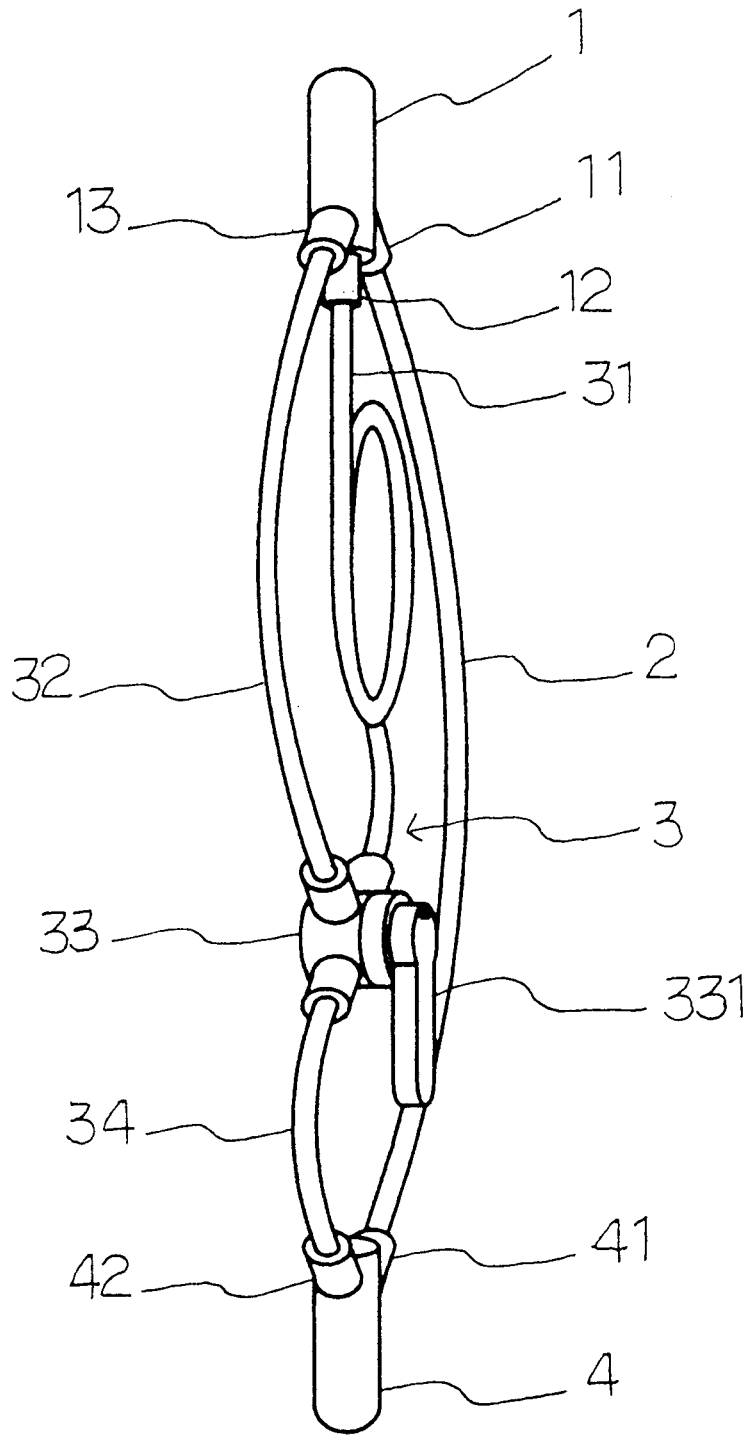
FIG. 1 is a perspective view showing an embodiment of the multi-stage type flow rate switching device of the present invention.

As shown by FIG. 1, a multi-stage flow rate switching device of the present invention includes a constant flow rate path 2 and a variable flow rate path 3. The paths are arranged in parallel between a liquid medicine flow inlet port 1 and a liquid medicine flow outlet port 4 and the flow rate of the variable flow rate path 3 can be changed by a three-way stopcock 33. Although the flow rate can be switched in four stages when the variable flow rate path 3 is arranged as shown by FIG. 1, the flow rate can be switched in further multi-stages by providing two or more of the variable flow rate paths 3 as necessary (refer to FIG. 4).

In the multi-stage flow rate switching device shown by FIG. 1, the liquid medicine flow inlet port 1 is branched into three branch paths 11, 12 and 13 and the liquid medicine flow outlet port 4 is branched into two branch paths 41 and 42. The constant flow rate path 2 is connected between the first branch path 11 of the liquid medicine flow inlet port 1 and the first branch path 41 of the liquid medicine flow outlet port 4. The variable flow rate path 3 is connected between the second branch path 12 and the third branch path 13 of the liquid medicine flow inlet port 1 and the second branch path 42 of the liquid medicine flow outlet port 4. The constant flow rate path 2 includes a flow rate control tube for controlling the flow rate by flow resistance. The entirety of the constant flow rate path 2 may be constituted by a flow rate control tube. The variable flow rate path 3 is constituted by the three-way stopcock 33, flow rate control tubes 31 and 32 respectively connected to the second branch path 12 and the third branch path 13 of the liquid medicine flow inlet port 1 and the three-way stopcock 33, and a connection tube 34 connected to the three-way stopcock 33 and the second branch path 42 of the liquid medicine flow outlet port 4 such that the flow rate can be varied by the three-way stopcock 33.

Figure 3:
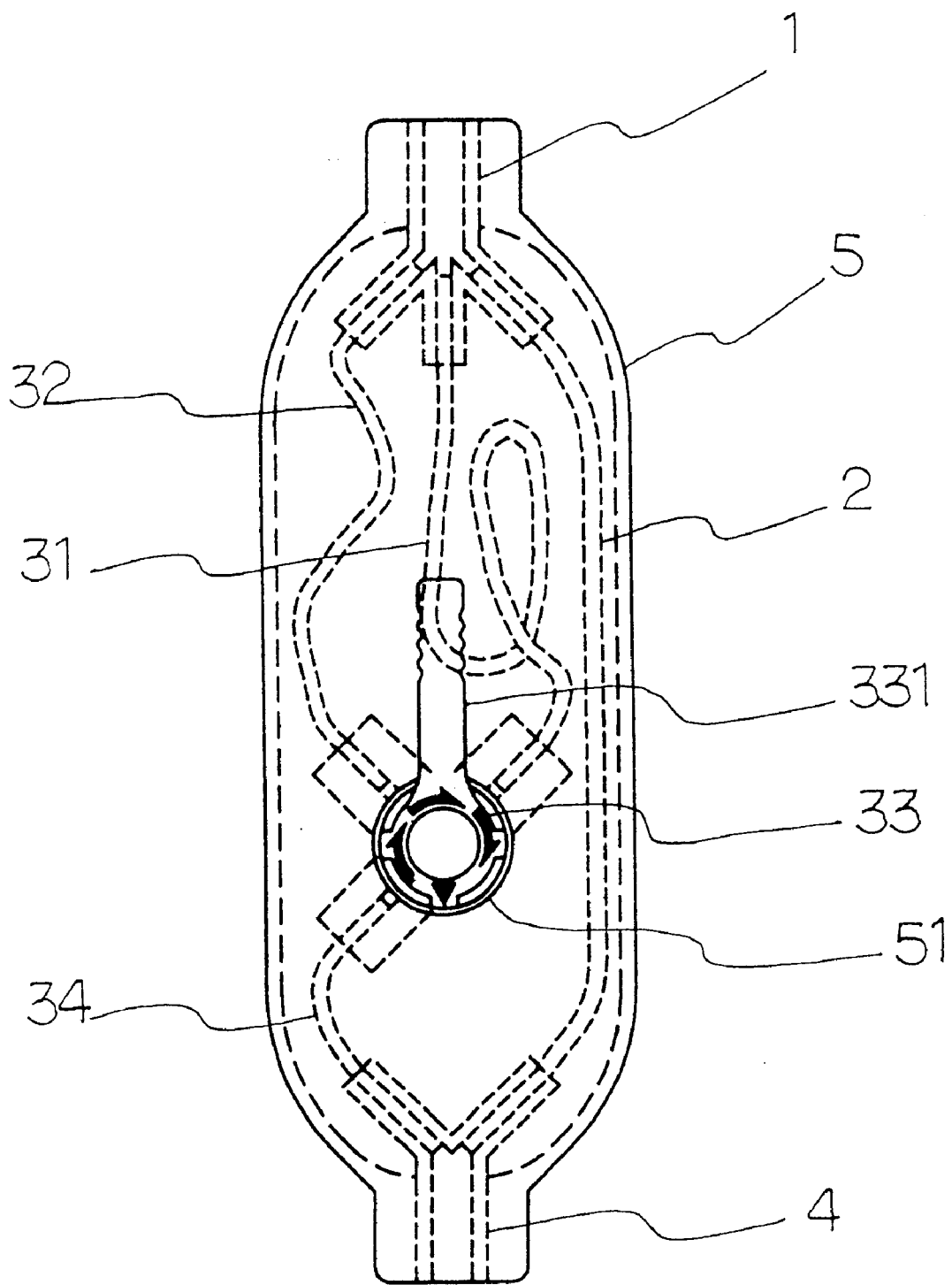
FIG. 3 is a plane view showing an embodiment of the multi-stage type flow rate switching device of the present invention incorporated in a housing.

The multi-stage type flow rate switching device may be constituted such that the liquid medicine flow inlet port 1 and the liquid medicine flow outlet port 4 are completely reversed in FIG. 1. That is, liquid medicine flows from the side of the liquid medicine flow outlet port 4 to the side of the liquid medicine flow inlet port 1 shown in FIG. 1. Also, the multi-stage type flow rate switching device may be constituted such that the device is accommodated in a housing 5 having a hole 51 for exposing a lever 331 of the three-way stopcock as shown in FIG. 3.

Two or more of the variable flow rate paths 3 may be assembled in parallel between a liquid medicine flow inlet port 1 and a liquid medicine flow outlet port 4 in the multi-stage type flow rate switching device.

Figure 4:
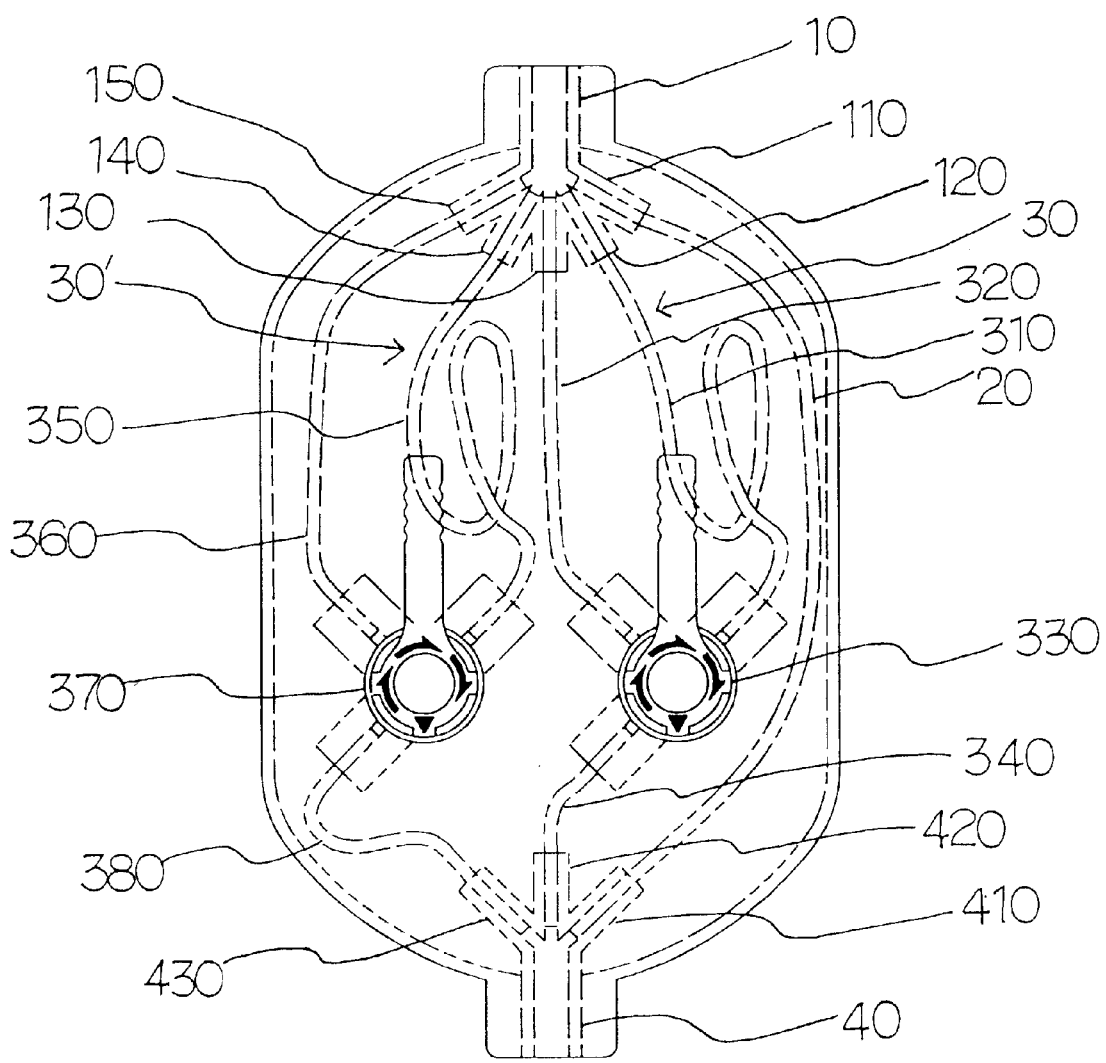
FIG. 4 is a plane view showing a second embodiment of the multi-stage type flow rate switching device of the present invention where two variable flow rate paths are assembled in parallel.

FIG. 4 illustrates an embodiment of the multi-stage type flow rate switching device of the present invention where two variable flow rate paths 30 and 30' are provided in parallel between a liquid medicine flow inlet port 10 and a liquid medicine flow outlet port 40.

In the multi-stage flow rate switching device shown in FIG. 4, the liquid medicine flow inlet port 10 is branched into five branch paths 110, 120, 130, 140 and 150 and the liquid medicine flow outlet port 40 is branched into three branch paths 410, 420 and 430. A constant flow rate path 20 is connected between the first branch path 110 of the liquid medicine flow inlet port 10 and the first branch path 410 of the liquid medicine flow outlet port 40. The first variable flow rate path 30 is connected between the second branch path 120 and the third branch path 130 of the liquid medicine flow inlet port 10 and the second branch path 420 of the liquid medicine flow outlet port 40. The second variable flow rate path 30' is connected between the fourth branch path 140 and the fifth branch path 150 of the liquid medicine flow inlet port 10 and the third branch path 430 of the liquid medicine flow outlet port 40.

The constant flow rate path 20 includes a flow rate control tube for controlling the flow rate by flow resistance. The entirety of the constant flow rate path 20 may be constituted by a flow rate control tube. The first variable flow rate path 30 is constituted by the three-way stopcock 330, flow rate control tubes 310 and 320 respectively connected to the second branch path 120 and the third branch path 130 of the liquid medicine flow inlet port 10 and the three-way stopcock 330, and a connection tube 340 connected to the three-way stopcock 330 and the second branch path 420 of the liquid medicine flow outlet port 40 such that the flow rate can be varied by the three-way stopcock.

The variable flow rate path 30' is constituted by the three-way stopcock 370, flow rate control tubes 350 and 360 respectively connected to the fourth branch path 140 and the fifth branch path 150 of the liquid medicine flow inlet port 10 and the three-way stopcock 370, and a connection tube 380 connected to the three-way stopcock 370 and the third branch path 430 of the liquid medicine flow outlet port 40 such that the flow rate can be further varied by the three-way stopcock 370.

The multi-stage type flow rate switching device of the present invention enables the flow rate of a liquid medicine to be set in multiple stages. For example, the flow rate can be switched in four stages when one variable flow rate path 3 is provided, and can be switched in sixteen stages when two of the variable flow rate paths 30 and 30' are provided.

Specifically, when the flow rates of the constant flow rate path 2 and the flow rate control tubes 31 and 32 of the variable flow rate path 3 in FIG. 1 are respectively set to, for example, 1 ml/hr, 1 ml/hr and 2 ml/hr, the flow rates can be set to four stages of 1 ml/hr, 2 ml/hr, 3 ml/hr and 4 ml/hr. When two of the variable flow rate paths are arranged as shown in FIG. 4, the flow rates can be set in sixteen stages of 1 ml/hr through 16 ml/hr by setting the flow rates of the constant flow rate path 20 and the flow rate control tubes 310, 320, 350 and 360 of the variable flow rate path 30 and 30' respectively to 1 ml/hr, 1 ml/hr, 2 ml/hr, 4 ml/hr and 8 ml/hr.

Figure 2:
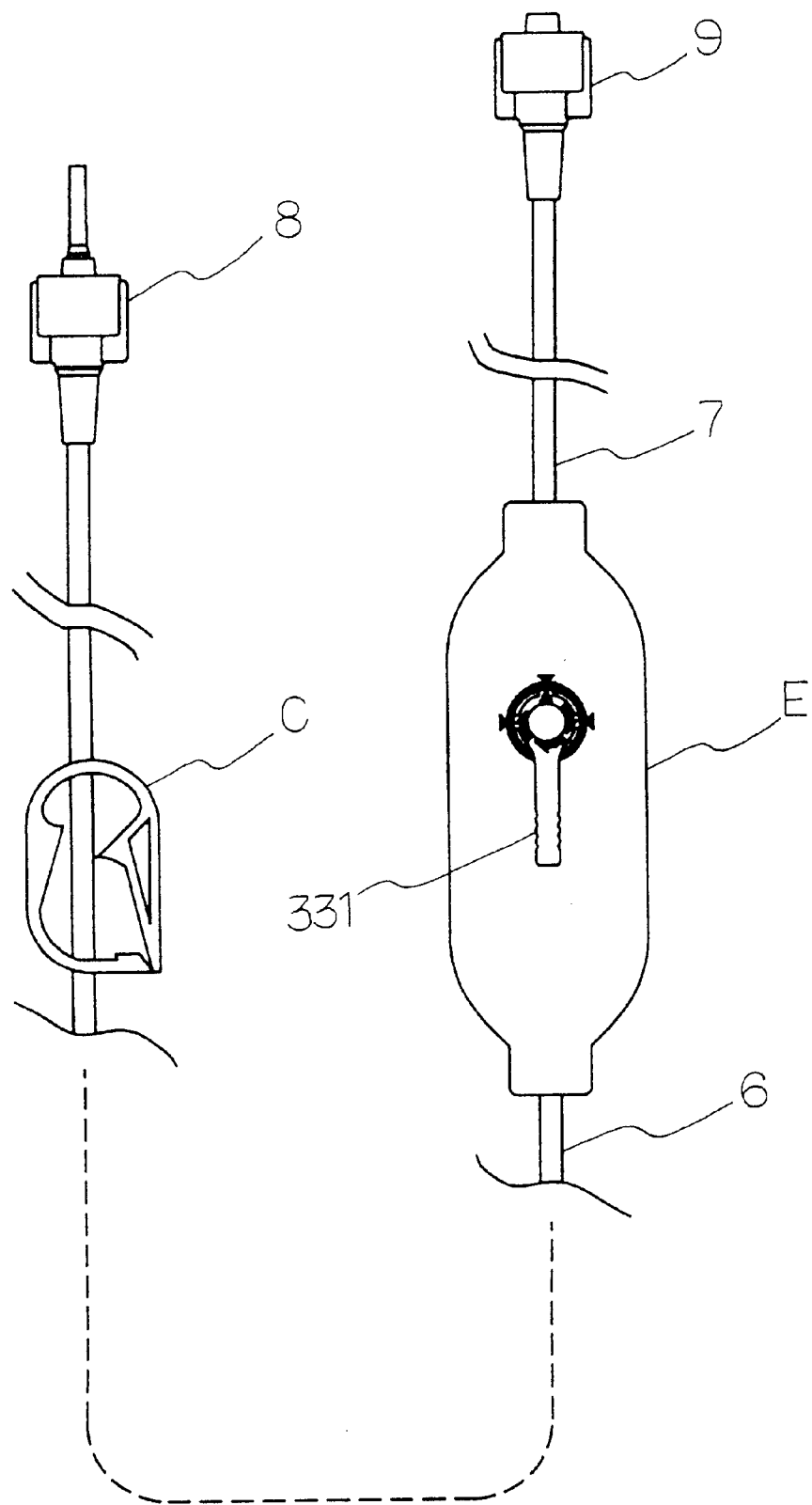
FIG. 2 illustrates an example of a liquid transfusion line integrated with a multi-stage type flow rate switching device of the present invention.

The multi-stage type flow rate switching device of the present invention is mainly used by being combined with a liquid transfusion line as shown in FIG. 2. In FIG. 2, notation E designates the multi-stage type flow rate switching device, notation C designates a clamp, numerals 6 and 7 designate connection tubes and numerals 8 and 9 designate connectors.

In using the liquid transfusion line, the connector 8 on the upstream side is connected to a liquid medicine injecting device, not shown, which utilizes the elastic force of a balloon, and the connector 9 on the downstream side is connected to a retaining needle, not shown. The clamp C is initially closed. When the clamp C is detached after setting the flow rate by operating the lever 331, a liquid medicine can be injected into blood vessels of a patient.

As apparent from the above-described explanation, the following effects can be achieved by adopting the flow rate control device of the present invention.

(1) Switching of the various flow rates is possible with the use of turning angles of 90° using combinations of the flow rate control tubes and the three-way stopcock and accordingly, a flow path switching operation is simplified and erroneous operation rarely occurs when a flow rate display is indicated on the housing.

(2) The three-way stopcock is accommodated in a housing and, accordingly, the flow path can not be switched by accident such as dropping or pressing of the flow rate switching device or the like.

What is claimed is:

1. A multi-stage type flow rate switching device comprising a liquid medicine flow inlet port; a liquid medicine flow outlet port; a constant flow rate path and at least one variable flow rate path connected to and arranged in parallel between said liquid medicine flow inlet port and said liquid medicine flow outlet port, said variable flow rate path constituted by two flow rate control tubes connected to one of said ports, a connetion tube connected to the other of said ports and a three-way stopcock connecting said two flow rate control tubes and said connection tube, the flow rate of a liquid medicine being changeable by the three-way stopcock.

2. The multi-stage type flow rate switching device according to claim 1, wherein said liquid medicine flow inlet port is branched into three branch paths, one of the branch paths and the two remaining branch paths are respectively connected to the constant flow rate path and the variable flow rate path and flow rate control tubes that control the flow rate of said liquid medicine by flow resistance are arranged in the constant flow rate path and the variable flow rate path.

3. The multi-stage type flow rate switching device according to claim 1, wherein the liquid medicine flow outlet port is branched into three branch paths, one of the branch paths and the two remaining branch paths are respectively connected to the constant flow rate path and the variable flow rate path and flow rate control tubes that control the flow rate of said liquid medicine by flow resistance are arranged in the constant flow rate path and the variable flow rate path.

4. The multi-stage type flow rate switching device according to claim 1, wherein the constant flow rate path and the variable flow rate path are accommodated in a housing having a liquid medicine flow inlet port and a liquid medicine flow outlet port at ends thereof.

5. The multi-stage type flow rate switching device according to claim 1, wherein at least two variable flow rate paths are connected and arranged in parallel between said liquid medicine flow inlet port and said liquid medicine flow outlet port, and a three-way stopcock is provided in each of said at least two variable flow rate paths for changing the flow rate of a liquid medicine through said device.

6. The multi-stage type flow rate switching device according to claim 2, wherein the constant flow rate path and the variable flow rate path are accommodated in a housing having a liquid medicine flow inlet port and a liquid medicine flow outlet port at ends thereof.

7. The multi-stage type flow rate switching device according to claim 3, wherein the constant flow rate path and the variable flow rate path are accommodated in a housing having a liquid medicine flow inlet port and a liquid medicine flow outlet port at ends thereof.

* * * * *